US010016248B2

(12) United States Patent
Mirsepassi et al.

(10) Patent No.: US 10,016,248 B2
(45) Date of Patent: Jul. 10, 2018

(54) OPHTHALMIC ILLUMINATION PROFILES AND ASSOCIATED DEVICES, SYSTEMS, AND METHODS

(71) Applicant: Novartis AG, Basel (CH)

(72) Inventors: Alireza Mirsepassi, Fort Worth, TX (US); Michael J. Papac, North Tustin, CA (US)

(73) Assignee: Novartis AG, Basel (CH)

( * ) Notice: Subject to any disclaimer, the term of this patent is extended or adjusted under 35 U.S.C. 154(b) by 95 days.

(21) Appl. No.: 14/973,287

(22) Filed: Dec. 17, 2015

(65) Prior Publication Data

US 2017/0172792 A1 Jun. 22, 2017

(51) Int. Cl.
*A61B 90/30* (2016.01)
*A61B 3/12* (2006.01)
*A61F 9/007* (2006.01)
*A61F 9/00* (2006.01)

(52) U.S. Cl.
CPC ............ *A61B 90/30* (2016.02); *A61B 3/1225* (2013.01); *A61F 9/007* (2013.01); *A61F 9/0008* (2013.01); *A61B 2090/306* (2016.02)

(58) Field of Classification Search
CPC ...... A61F 9/007; A61F 9/0008; A61F 9/0017; A61B 2090/306; A61B 90/30; A61B 3/1225
USPC .............. 351/221; 606/4, 107; 604/264, 506
See application file for complete search history.

(56) References Cited

U.S. PATENT DOCUMENTS

| | | | |
|---|---|---|---|
| 2005/0099824 A1 | 5/2005 | Dowling et al. | |
| 2006/0245702 A1* | 11/2006 | Cazzini | A61B 1/00165 385/115 |
| 2007/0100327 A1 | 5/2007 | Smith | |
| 2008/0246920 A1 | 10/2008 | Buczek et al. | |
| 2009/0182313 A1* | 7/2009 | Auld | A61B 17/28 606/15 |
| 2010/0182569 A1 | 7/2010 | Artsyukhovich et al. | |
| 2011/0110114 A1 | 5/2011 | Papac et al. | |
| 2012/0041461 A1* | 2/2012 | McCollam | A61F 9/00736 606/170 |
| 2012/0050684 A1* | 3/2012 | Smith | A61B 3/0008 351/221 |
| 2012/0283523 A1* | 11/2012 | Yadlowsky | A61F 9/00763 600/249 |
| 2013/0077917 A1 | 3/2013 | Lassalas et al. | |
| 2013/0079598 A1 | 3/2013 | Auld et al. | |

(Continued)

*Primary Examiner* — Jordan Schwartz
(74) *Attorney, Agent, or Firm* — S. Latimer Brannon (57) ABSTRACT

An ophthalmic illumination apparatus can include a body sized and shaped for grasping by a user. The apparatus can also include a cannula coupled to the body and configured to be positioned within an eye of a patient. The apparatus can further include a first optical fiber disposed within the cannula. The first optical fiber can be configured to transmit light having a first angular profile. The apparatus can also include a second optical fiber disposed within the cannula. The second optical fiber is configured to transmit light having a second angular profile. A method of surgical illumination can include illuminating an eye of a patient with light having a first angular profile. The method can also include illuminating the eye of the patient with light having a second angular profile. The different angular profiles can be transmitted by different optical fibers disposed within a cannula positioned within the eye.

13 Claims, 9 Drawing Sheets

(56) References Cited

U.S. PATENT DOCUMENTS

| | | | |
|---|---|---|---|
| 2014/0180264 A1* | 6/2014 | Diao .................. | A61F 9/00823 |
| | | | 606/4 |
| 2015/0327945 A1* | 11/2015 | Schaeffer .......... | A61B 1/00165 |
| | | | 600/249 |
| 2016/0051335 A1 | 2/2016 | Richmond | |
| 2016/0058614 A1* | 3/2016 | Ross ...................... | A61F 9/007 |
| | | | 606/107 |
| 2017/0127983 A1* | 5/2017 | Spegazzini .......... | A61B 5/1495 |

* cited by examiner

OPHTHALMIC ILLUMINATION PROFILES AND ASSOCIATED DEVICES, SYSTEMS, AND METHODS

BACKGROUND

Technical Field

Embodiments disclosed herein can be related to ophthalmic illumination systems. More specifically, embodiments described herein can relate to illuminating a surgical field, such as a patient's eye, with light having different angular profiles transmitted by multiple optical fibers of an illumination device.

Related Art

Ophthalmic microsurgical procedures can require precision cutting and/or removing of various body tissues of the patient's eye. During a surgical procedure, a user, such as a surgeon or other medical professional, can hold an endo-illuminator or an endo-illumination probe in one hand. During a vitrectomy procedure, for example, the surgeon can hold a vitrectomy probe in his or her other hand. The vitrectomy probe can be used to perform surgical maneuvers while the surgeon visualizes the patient's eye using the light provided by the endo-illuminator. The endo-illuminator can include a cannula inserted into the eye and an optical fiber approximately equal to the diameter of the cannula. Because endo-illuminators typically transmit wide-angle light, options for modifying the type of illumination within the eye can be limited.

Accordingly, there remains a need for improved devices, systems, and methods that allow the surgeon to illuminate the patient's eye with light having different angular profiles by addressing one or more of the needs discussed above.

SUMMARY

The presented solution fills an unmet medical need with a unique solution to output light having different angular profiles into the patient's eye during an ophthalmic surgical procedure. An illumination apparatus can include multiple optical fibers positioned within a cannula. The cannula can be inserted into the patient's eye. The optical fibers can be sized and shaped to respectively transmit light having different angular profiles. For example, one optical fiber can transmit light for wide-field illumination to provide general situational awareness for a surgeon during the surgical procedure. A second optical fiber can transmit light for narrow-field illumination. Narrow-field illumination can allow the surgeon to visualize anatomy within the patient's eye, such as vitreous humor. The surgeon can toggle between the multiple angular profiles of light depending the surgeon's visualization needs during the surgical procedure.

Consistent with some embodiments, an ophthalmic illumination apparatus can be provided. The apparatus can include a body sized and shaped for grasping by a user. The apparatus can also include a cannula coupled to the body and configured to be positioned within an eye of a patient. The apparatus can further include a first optical fiber disposed within the cannula. The first optical fiber can be configured to transmit light having a first angular profile. The apparatus can also include a second optical fiber disposed within the cannula. The second optical fiber is configured to transmit light having a second angular profile.

Consistent with some embodiments, a method of ophthalmic surgical illumination can be provided. The method can include illuminating an eye of a patient with light having a first angular profile. The light having the first angular profile can be transmitted by a first optical fiber disposed within a cannula positioned within the eye. The method can also include illuminating the eye of the patient with light having a second angular profile. The light having the second angular profile can be transmitted by a second optical fiber disposed within the cannula.

Additional aspects, features, and advantages of the present disclosure will become apparent from the following detailed description.

BRIEF DESCRIPTION OF THE DRAWINGS

In the drawings, elements having the same designation have the same or similar functions.

DETAILED DESCRIPTION

In the following description, specific details can be set forth describing certain embodiments. It will be apparent, however, to one skilled in the art that the disclosed embodiments may be practiced without some or all of these specific details. Specific and/or illustrative, but not limiting, embodiments can be presented herein. One skilled in the art will realize that other material, although not specifically described herein, can be within the scope and spirit of this disclosure.

The present disclosure describes devices, systems, and methods of selectively illuminating a surgical field, such as a patient's eye, with light having different angular profiles. For example, a surgeon can choose to have wide-field, narrow-field, and/or other types of illumination during an ophthalmic surgical procedure. Two or more optical fibers can be positioned within a cannula of an ophthalmic illumination apparatus. The cannula can be inserted into the patient's eye. The optical fibers can be differently sized and shaped such that they emit light having different angular profiles. For example, a distal portion of the optical fibers can be tapered or include a scattering tip. The surgeon can choose which optical fiber emits light during the surgical procedure depending on the desired angular profile. The cannula can be deflected such that a desired area, such as the periphery of the eye, can be illuminated. The cannula can be articulated to facilitate such deflection. An optical fiber transmitting a therapeutic laser beam and an endoscopy fiber bundle can also be positioned within the cannula of the illumination device.

The devices, systems, and methods of the present disclosure provide numerous advantages, including: (1) increased control of intra-operative illumination for the surgeon; (2) improved operating conditions for the surgeon with the ability to adjust retinal glare; (3) enhanced visualization of anatomy, such as the vitreous humor, for the surgeon using narrow-angle illumination, while preserving situational awareness for the surgeon using medium-angle and/or wide-angle illumination; (4) increased illumination area within the patient's eye with cannula deflection; and (5) improved working conditions for surgeon with incorporation of multiple fibers for illumination, treatment, and/or endoscopy into a single device.

Figure 1:
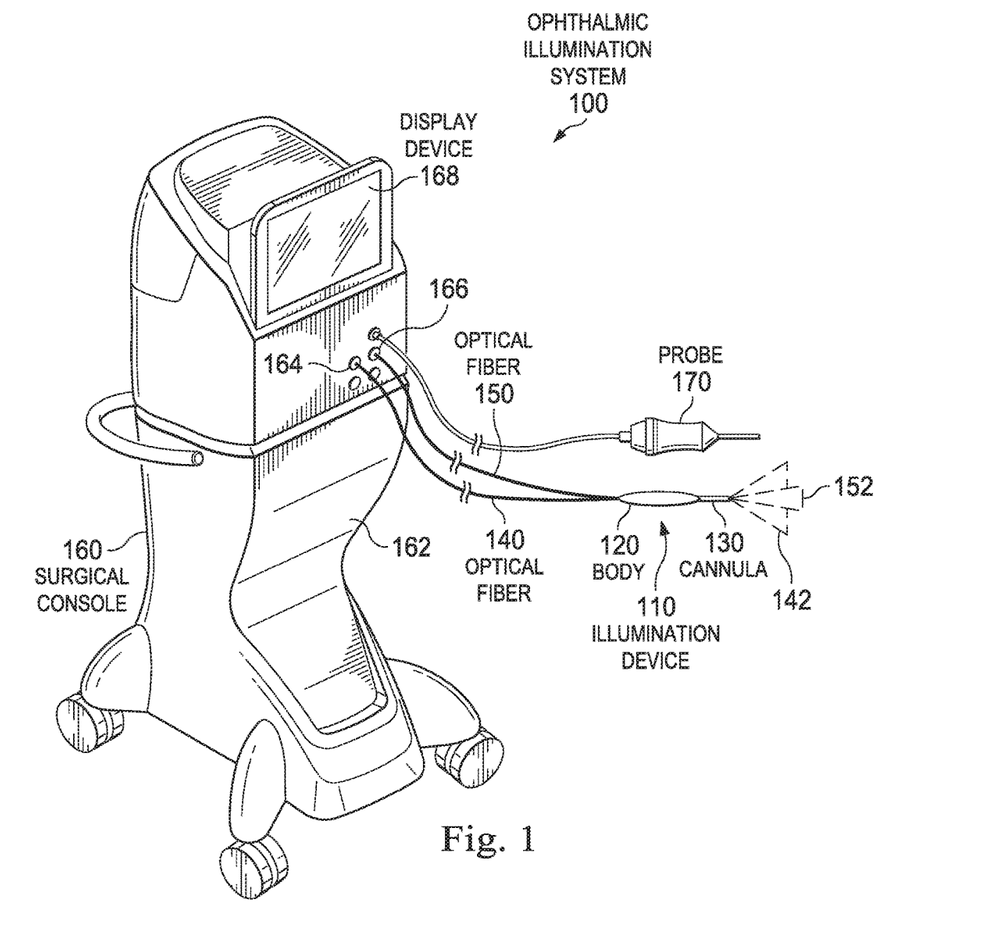
FIG. 1 is an illustration of an ophthalmic illumination system.
Figure 2:
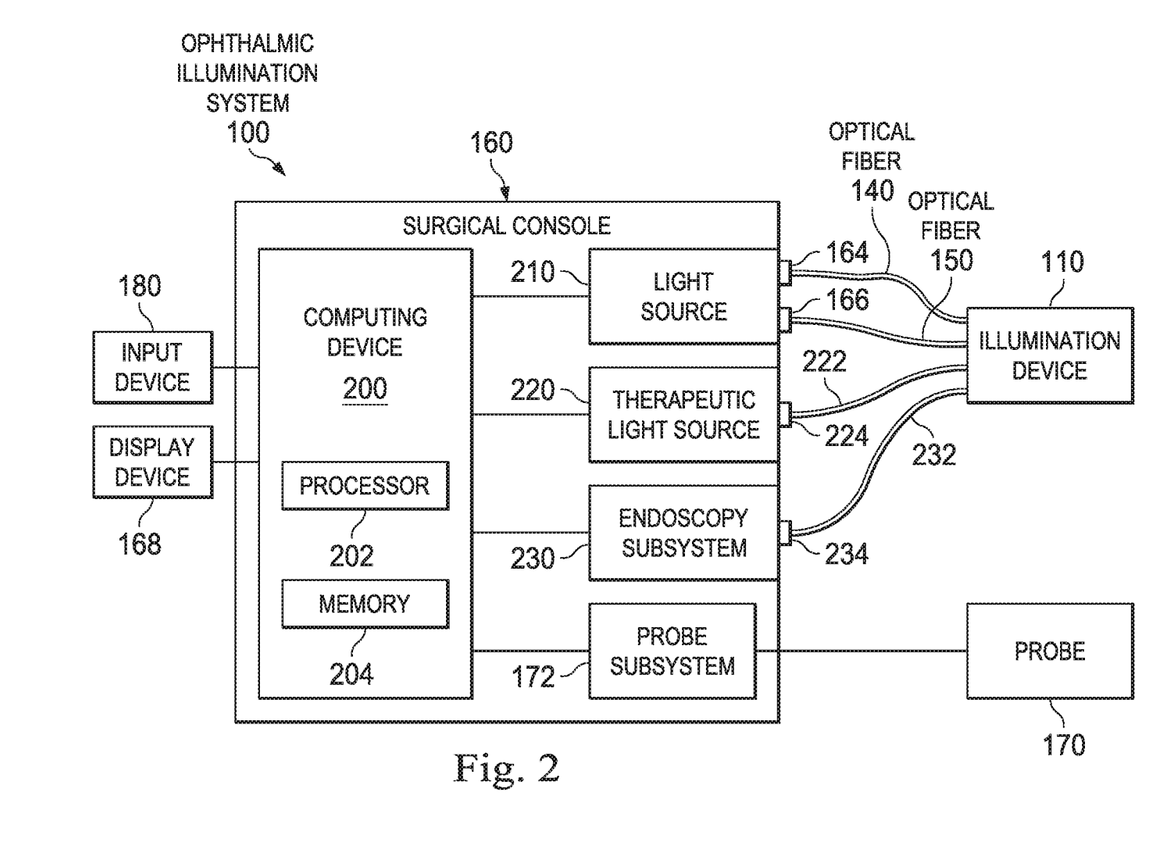
FIG. 2 is a schematic diagram illustrating an ophthalmic illumination system.
Figure 3:
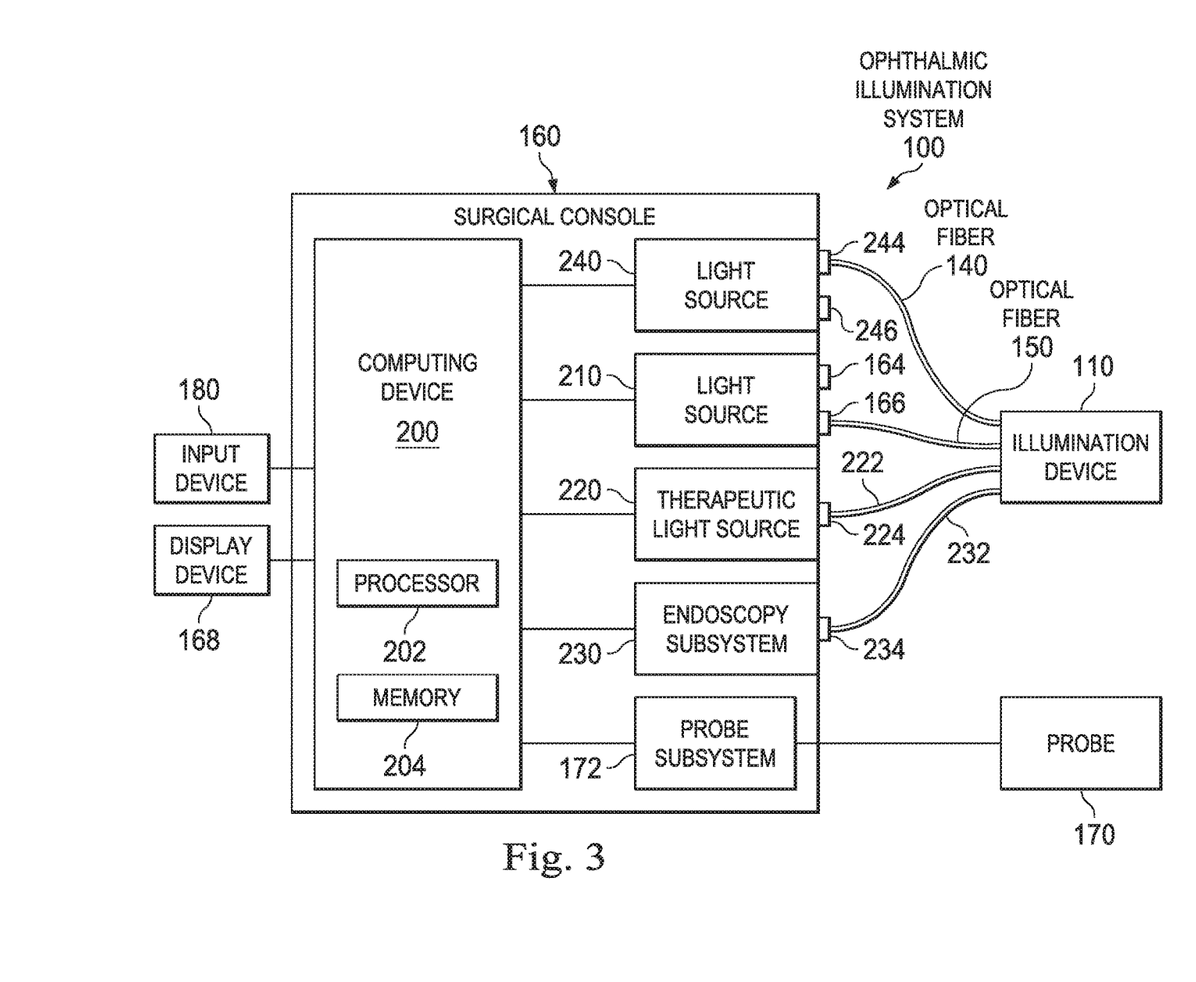
FIG. 3 is a schematic diagram illustrating an ophthalmic illumination system.
Figure 7:
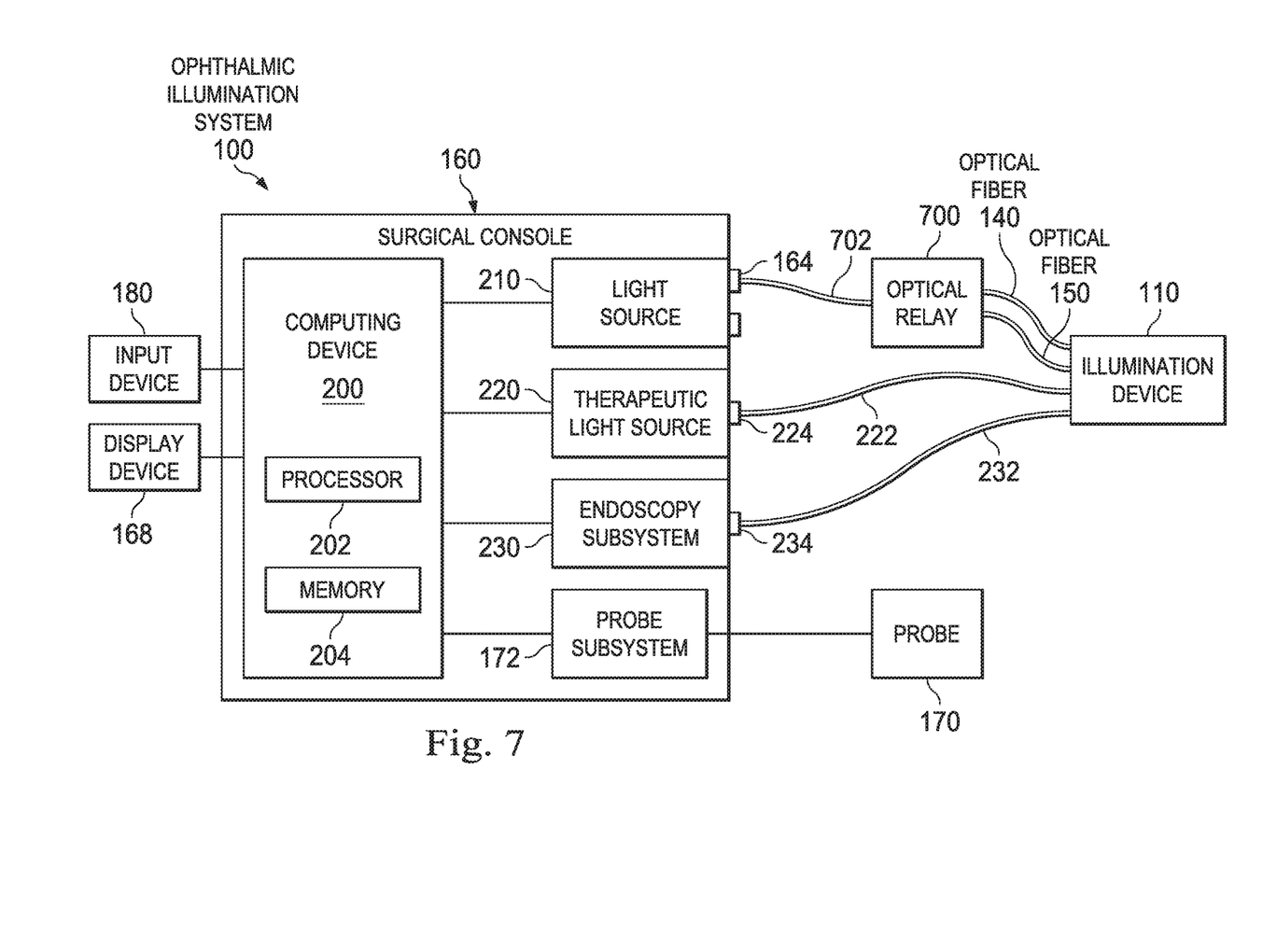
FIG. 7 is a schematic diagram illustrating an ophthalmic illumination system.

FIGS. 1, 2, 3, and 7 illustrate an example ophthalmic illumination system 100. FIG. 1 can be an illustration of the ophthalmic illumination system 100. FIGS. 2, 3, and 7 can be schematic diagrams of the ophthalmic illumination system 100. The ophthalmic illumination system 100 can include an illumination device 110 having a body 120 and a cannula 130. The body 120 can be sized and shaped for grasping by a user. The cannula 130 can be coupled to the body. The cannula 130 can be configured to be positioned within a surgical field, such as a patient's eye. The illumination device 110 can include optical fibers 140, 150 disposed within the cannula 130. The optical fiber 140 can be configured to transmit light 142 having an angular profile, and the optical fiber 150 can be configured to transmit light 152 having another angular profile. As described herein, the angular profiles of the light 142, 152 can be different or substantially similar. The optical fibers 140, 150 can be configured to selectively illuminate the patient's eye.

The ophthalmic illumination system 100 can be used to perform various ophthalmic surgical procedures including an anterior segment procedure, a posterior segment procedure, a vitreoretinal procedure, a vitrectomy procedure, a cataract procedure, and/or other desired procedures. The user, such as a surgeon or other medical professional, can operate the illumination device 110 to illuminate the surgical field. The surgical field can include any suitable physiology of the patient's eye, including a lens, a vitreous chamber, transparent membranes, blood vessels, a retina, a macula, a foveola, a fovea centraalis, a para fovea, a perifovea, an optic disc, an optic cup, and/or other biological tissue.

Figure 8:
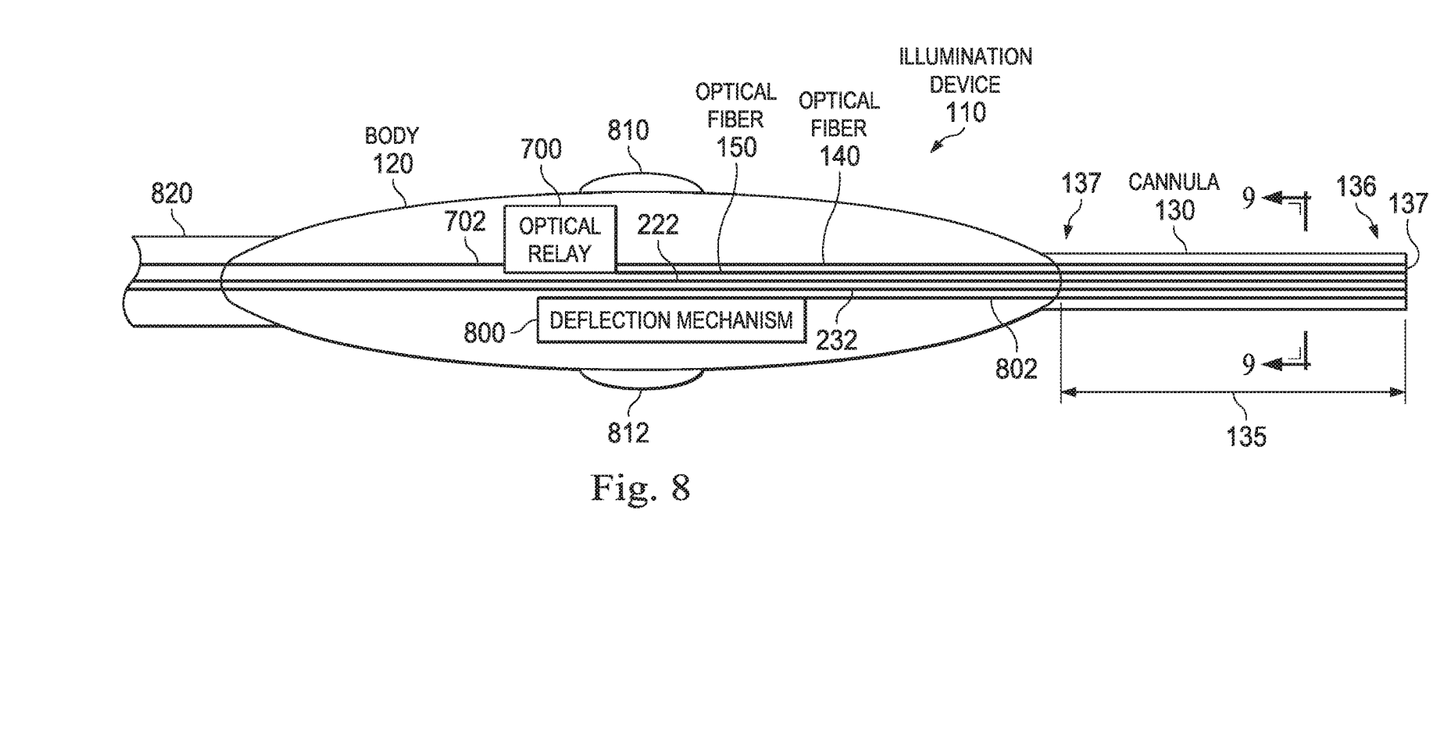
FIG. 8 is an illustration of an illumination device.

Referring to FIGS. 1 and 8, the body 120 of the illumination device 110 can form a handle for the illumination device 110. FIG. 8 can be cross-sectional, side-view illustration of the illumination device 110. The body 120 can be sized and shaped for handheld use and/or grasping by the user. For example, the body 120 can be any suitable shape, including ellipsoidal, polygonal, tubular, other desired shapes, and/or combinations thereof. The body 120 can be made of any suitable material, such as a thermoplastic or metal. The body 120 can be formed by any method, including, for example, injection molding or machining. At least a portion of the body 120 can be knurled, patterned, and/or otherwise textured to improve gripping. The body 110 can be formed of two or more sections joined together. The body 110 can include one, two, three, or more controls 810, 812. The controls 810, 812 can be buttons, sliders, toggles, wheels, other suitable actuatable components, and/or combinations thereof. The controls 810, 812 can be used to control various functions of the illumination device 110 described herein. In that regard, the controls 810, 812 can be an input device 180 as further described herein.

Figure 4A:
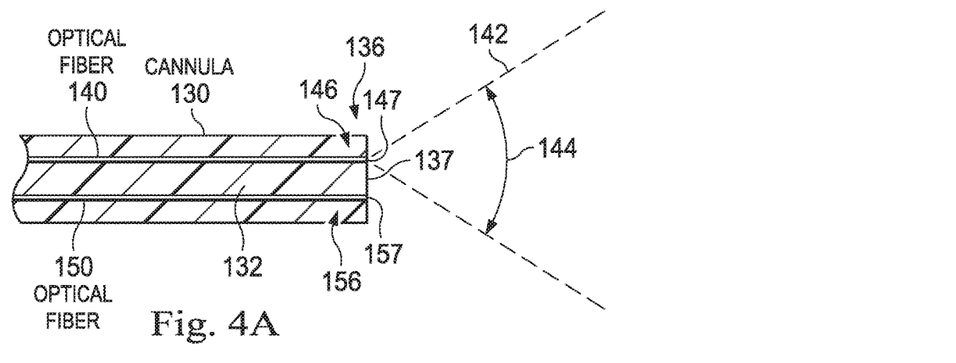
FIGS. 4A and 4B are illustrations of a cannula of an illumination device.
Figure 4B:
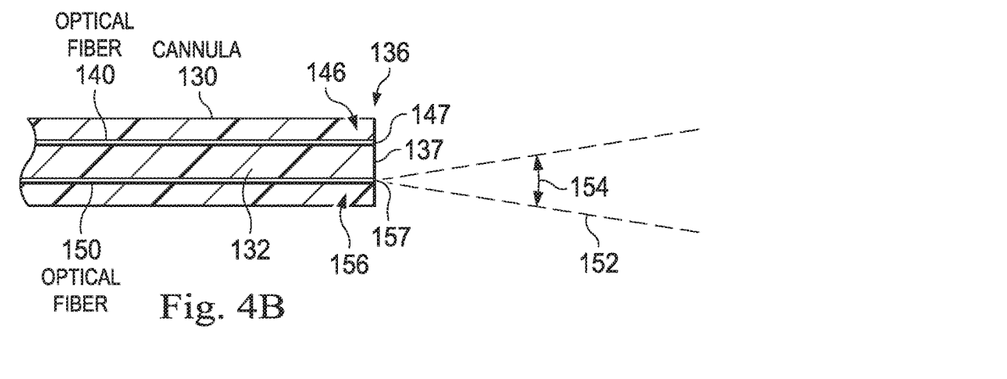
Figure 6:
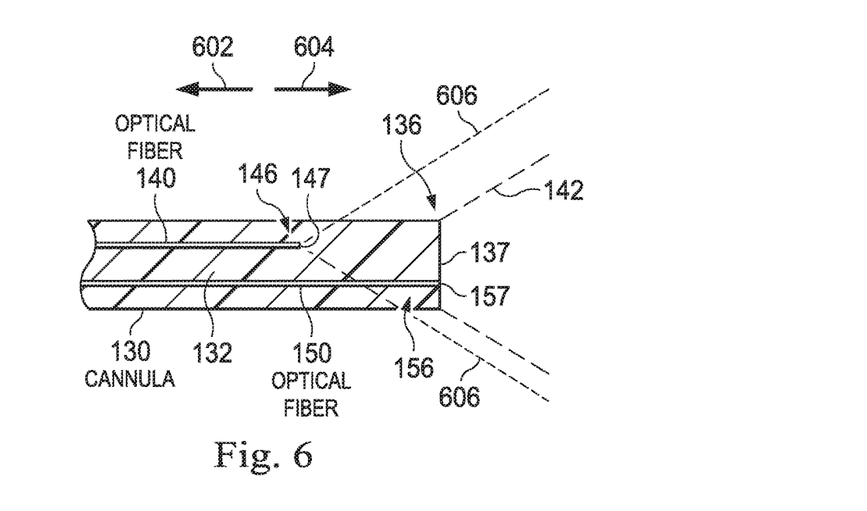
FIG. 6 is an illustration of a cannula of an illumination device.
Figure 9:
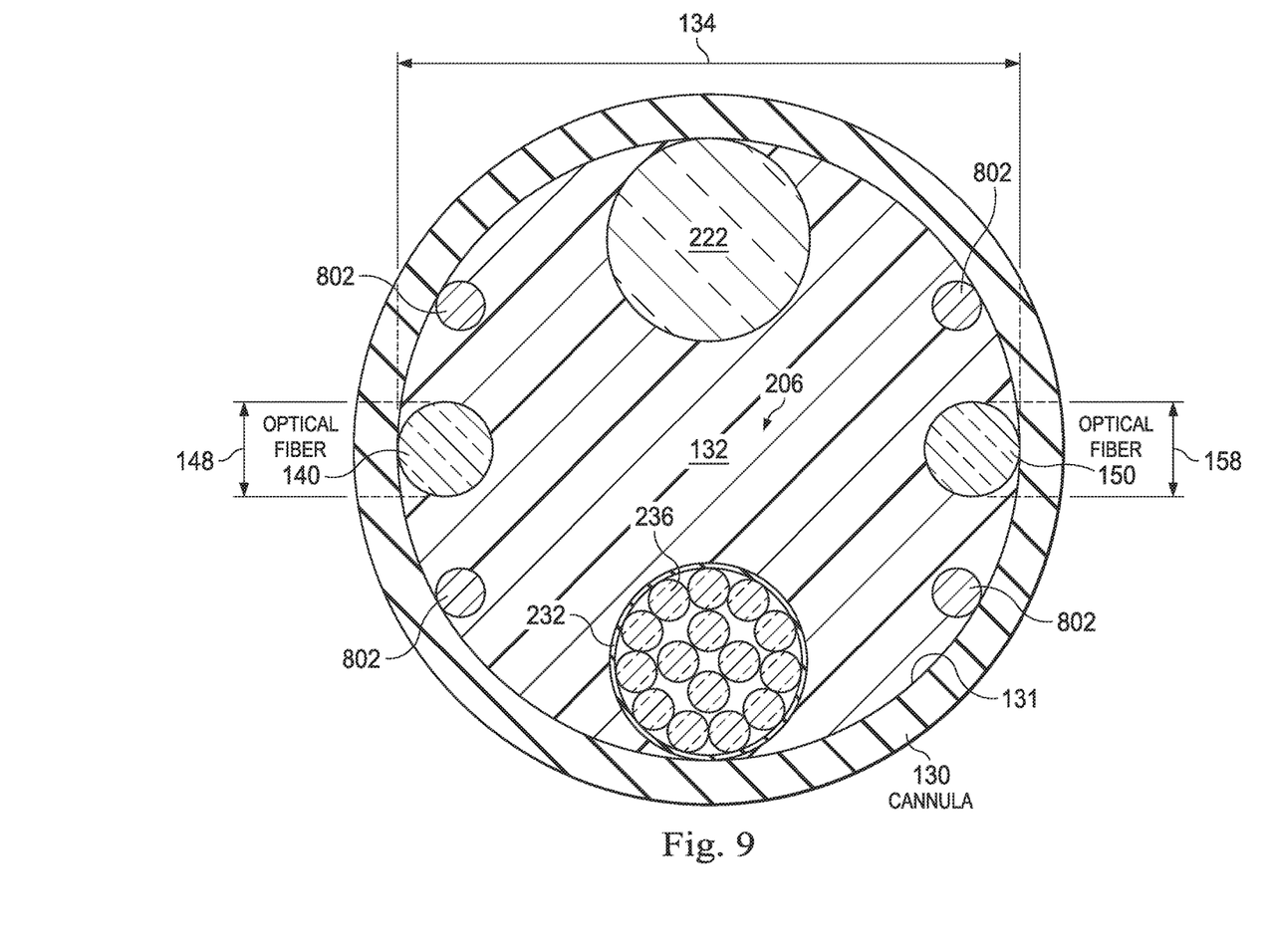
FIG. 9 is a cross-sectional end view illustration of a cannula of an illumination device.

Referring to FIGS. 1, 4A, 4B, 6, 8, and 9, the cannula 130 of the illumination device 110 can extend from the body 120. FIGS. 4A, 4B, and 6 can be cross-sectional, side-view illustrations of the cannula 130. FIG. 9 can be a cross-sectional, end view of the cannula 130 taken along the section line 9-9 of FIG. 8. The cannula 130 can include a lumen 132, a distal portion 136, and a proximal portion 137.

The cannula 130 can be coupled to the body 120 at the proximal portion 137. The cannula 130, including the distal portion 136, can be sized and shaped for insertion into an interior space of the eye, such as the vitreous chamber. The cannula 130 can be any suitable medical grade tubing, such as titanium, stainless steel, or suitable polymer. The cannula can be any desired size, including 27 G, 25 G, and 23 G, and/or other suitable values, both larger and smaller. The cannula 130 can have an internal diameter 134 and a length 135. The internal diameter 134 can be between approximately 400 microns and approximately 600 microns, between approximately 400 microns and approximately 550 microns, between approximately 400 microns and approximately 500 microns, and/or other suitable values, both larger and smaller. The length 135 of the cannula 120 can be between approximately 20 mm and approximately 50 mm, between approximately 20 mm and approximately 40 mm and/or other suitable values, both larger and smaller. The cannula 120 can have a cross-section shaped as a polygon, an ellipse, other suitable shape, and/or a combination thereof. For example, the cannula 120 can be cylindrically-shaped so as to have a circular cross-section.

The illumination device 110, the body 120, and/or the cannula 130 can be disposable or configured for a single use. In other examples, illumination device 110, the body 120, and/or the cannula 130 can be sterilizable and configured for multiple uses. For example, the illumination device 110, the body 120, and/or the cannula 130, can be autoclavable and/or otherwise sterilizable.

Two or more optical fibers 140, 150 can be disposed within the lumen 132 of the cannula 130. While the description herein may refer to two optical fibers 140, 150, any suitable number of optical fibers, including three, four, or more can be implemented in the illumination device 110. In some cases, an optical fiber bundle having any suitable number of fibers, including one, two, three, four, or fibers, can be positioned within the cannula 130. The optical fibers 140, 150 can include a core, a cladding, and a coating, and/or other layer(s). The core of the optical fibers 140, 150 can be a cylinder of glass, plastic, silica, and/or other suitable material through which light propagates. The cladding can surround the core and confine the light within the core 202. The cladding can include a dielectric material with an index of refraction less than the index of refraction of the core. The coating can surround the cladding and protect the optical fibers 140, 150 from physical damage. As illustrated in FIG. 9, the optical fiber 148 can have a diameter 148, and the optical fiber 150 can have a diameter 158. The diameter 148 and/or the diameter 158 can between approximately 30 microns and approximately 50 microns, between approximately 30 microns and 45 microns, between approximately 35 microns and approximately 50 microns, including values such as 30 microns, 35 microns, 40 microns, 45 microns, 50 microns, and/or other suitable values, both larger and smaller.

As illustrated in FIGS. 1, 4A, and 4B, the optical fiber 140 can emit light 142 into the surgical field, and the optical fiber 150 can emit light 152 into the surgical field. For example, wherein the input device 180 can be receive a user input to cause the optical fiber 140 and/or the optical fiber 150 to selectively illuminate the eye of the patient. The angular profiles of the light 142, 152 can be different. For example, the light 142 can provide wide-field illumination. Wide-field illumination can facilitate the user's situational awareness within the surgical field while performing various surgical maneuvers. The light 152 can provide narrow-field illumination. Narrow-field illumination can have a relatively higher irradiance compared to wide-field illumination. The higher irradiance of narrow-field illumination can allow the user to see anatomy within the eye that may not be clearly visible with wide-field illumination. For example, the vitreous humor, the clear jelly that fills the posterior segment of the patient's eye, can be more clearly visualized using narrow-field illumination. The user can selectively utilize narrow-field illumination to view the vitreous humor, for example, during vitrectomy procedure. By controlling if the optical fiber 140 or the optical fiber 150 transmits light, the user can switch between wide-field and narrow-field illumination based on the surgical tasks being performed. Generally, a cone angle 144 of the light 142 and a cone angle 154 of the light 152 can be between approximately 1° and approximately 170°, between approximately 45° and approximately 160°, between approximately 90° and approximately 160°, including values such as 90°, 120°, 135°, and/or other suitable values, both larger and smaller.

Figure 5A:
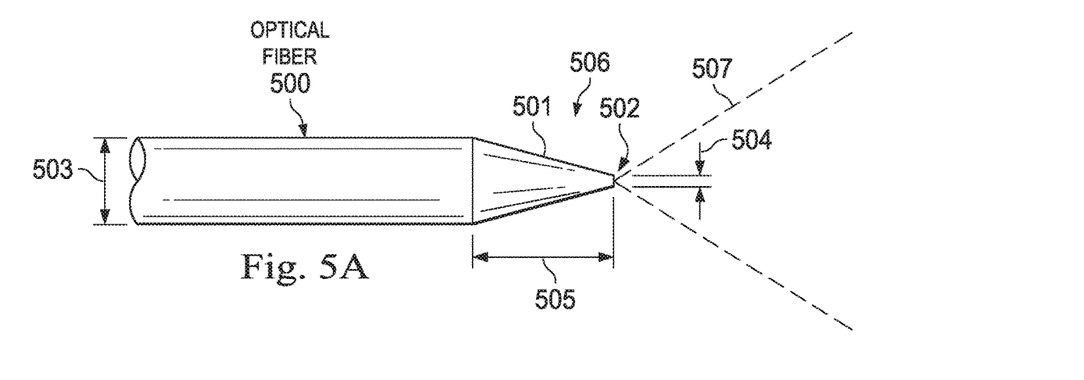
FIGS. 5A, 5B, 5C, 5D, and 5E are illustrations of an optical fiber of an illumination device.
Figure 5B:
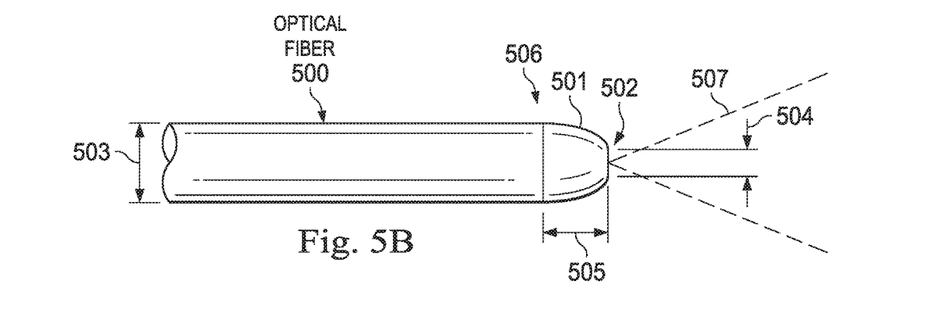
Figure 5C:
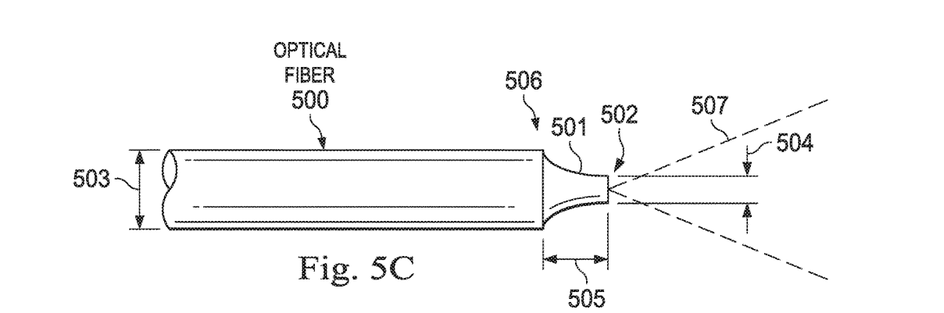

FIGS. 5A-5E illustrate side views of an optical fiber 500 including a distal portion 506 that transmits light 507 having different angular profiles. The optical fiber 500 can be substantially similar to the optical fibers 140, 150 described herein. A diameter 503 of the optical fiber 500 can be similar to the diameter 148 of the optical fiber 140 and/or the diameter 158 of the optical fiber 150. The distal portion 506 of the optical fiber 500 can include a tip 502. FIGS. 5A-5C illustrates that the distal portion 506 can include a taper 501. The size, shape, and/or other parameters of the taper 501 can determine the angular profile of the light 507. For example, the taper 501 can be linear (FIG. 5A), concave (FIG. 5B), or convex (FIG. 5C). Angular content of the light can get controlled by the shape of the taper. Various mathematical methods, such as Monte Carlo simulation, can be used to determine the effect the shape of the taper 501 has on the angular content of light. A length 505 of the taper 501 can also determine the angular profile of the light 507. A longer taper length can generally causes a more effective angular broadening (adiabatic taper), which corresponds to higher forward efficiency. A taper ratio of the taper 501 can also determine the angular profile. A taper ratio can be a ratio of the diameter 504 of the tip 502 to the diameter 503 of the optical fiber 500. A mathematical relationship can describe the diameter and the angular spread of light beam within the optical fiber 500. A numerical aperture can be quantity describing the angular spread. The product of the numerical aperture and the beam diameter can be constant. With a relatively smaller beam diameter, such as with a relatively smaller diameter 504 of the tip 502, the numerical aperture of the light can be relatively larger. As a result, the angular profile of the light 507 can be wider. With a relatively larger beam diameter, such as with a relatively larger diameter 504 of the tip 502, the numerical aperture of the light can be relatively smaller. As a result, the angular profile of the light 507 can be narrower.

Figure 5D:
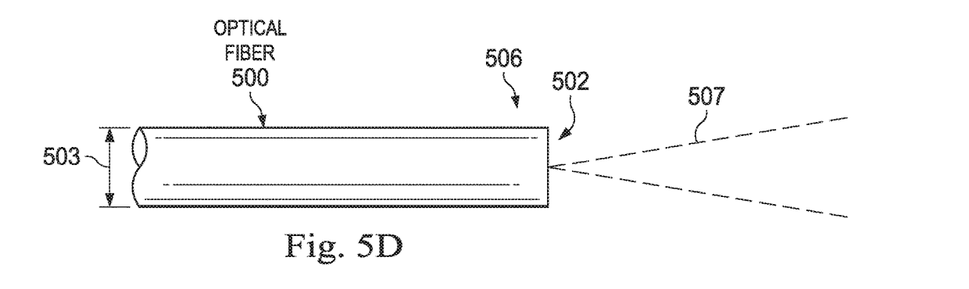

The distal portion 506 of the optical fiber 500 in FIG. 5D can be cleaved. The distal portion 506 can be similarly sized and shaped to more proximal portions of the optical fiber 500. The angular profile of the light 507 can be relatively narrow in such a configuration of the optical fiber 500.

Figure 5E:
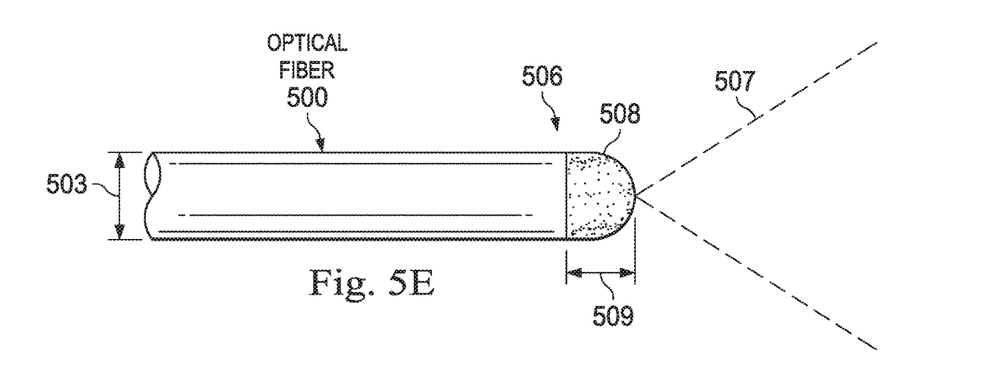

The distal portion 506 of the optical fiber 500 in FIG. 5E can include a scattering tip 508. Generally, any suitable method of creating a refractive index gradient can be implemented in the scattering tip 508 to cause light scattering. For example, the scattering tip 508 can include embedded particles that interact with the light transmitted by the optical fiber 500. The light 507 emitted from the optical fiber 500 can have a relatively wider angular profile with a scattering tip 508. The size, shape, and/or other parameters of the scattering tip 508 can determine the scattering properties of the light 507. The parameters influencing the scattering properties of the light 507 can include the refractive index of material(s) forming the scattering tip 508, and the size and volume fraction of the particles embedded or features in the scattering tip 508. By increasing the size and volume fraction of particles, the scattering increases. Scattering can also increase when the refractive index gradient between the particle or features increases with respect to the media. The amount of scattering can be selected to maintain an acceptable amount of forward efficiency for the instrument. A length 509 of the scattering tip 508 can also determine the angular profile of the light 507. By increasing the length 509, the scattering can increase. The parameter(s) can be chosen to achieve an efficient forward scattering scenario. The distal portion 506 of the optical fiber 500 can also include a diffusion coating configured to widen the angular profile of the light 507.

Referring again to FIGS. 4A, 4B, 8, and 9, the optical fibers 140, 150 can be coupled to the cannula 130. As illustrated in FIG. 9, for example, the optical fibers 140, 150 can be coupled an inner wall 131 of the cannula 130. The optical fiber 140 and/or the optical fiber 150 can be fixedly coupled such that the optical fibers 148, 158 do not move with respect to the cannula 130. Any suitable coupling, including an adhesive, a mechanical structure, and/or combinations thereof, can be implemented. A distal portion 146 of the optical fiber 140 and a distal portion 156 of the optical fiber 150 can be aligned with the distal portion 136 of the cannula 130. For example, a distal end 147 of the optical fiber 140 and/or a distal end 157 of the optical fiber 150 can be laterally aligned with a distal end 137 of the cannula 130. In that regard, the distal ends 137, 147, 157 can be coplanar. The optical fibers 140, 150 can be positioned relative to the cannula 130 such that the cannula 130 impedes none of the light 142, 152.

Referring to FIG. 6, the optical fiber 140 and/or the optical fiber 150 can be movably coupled to the cannula 130. For example, the optical fibers 140, 150 can be translatable with respect to the cannula 130. Any suitable coupling, such as a mechanical structure, can be implemented. The optical fibers 140, 150 can selectively move laterally with respect to the cannula 130 in directions 602, 604. For example, the user can provide a user input at the input device 180 (FIG. 2), such as the controls 810 or 812 (FIG. 8), a surgical footswitch, or controls integrated in a surgical console 160. The input device 180 can be in communication with the illumination device 110 such that the optical fibers 140, 150 are translated in the directions 602, 604 in response to the user input. Thus, the distal ends 147, 157 of the optical fibers 140, 150, respectively, can be positioned proximal of, distal of, or aligned with the distal end 137 of the optical cannula 130. In that regard, the distal ends 147, 157 of the optical fibers 140, 150, respectively, can be spaced from the distal end 137 of the optical fiber 130. The user can control an angular divergence of the light 142 by selectively translating the optical fibers 140, 150. For example, as illustrated, the optical fiber 140 can be translated in the direction 602. The distal end 137 of the cannula 130 can be positioned distally beyond the distal end 147 of the optical fiber 140. A portion 606 of the light 142 can be blocked by the cannula 130. As a result, the light 142 can have a relatively smaller angler divergence compared to the angular divergence if the distal end 147 of the optical fiber 140 and the distal end 137 of the cannula 130 were aligned.

The optical fibers 140, 150 can be coupled to one or more light sources configured to output light to illuminate the surgical field. Referring to FIG. 2, the optical fibers 140, 150 can be coupled to a light source 210. The light source 210 can include ports 164, 166. Light output by the light source 210 can be selectively directed to the port 164 or the port 166. The light source 210 can include a beam director to selectively guide the light to the port 164 or the port 166. For example, the user can select which of the optical fibers 140, 150 transmit light to the surgical field based on which of the ports 164, 166 the light source 210 provides light to. The light source 210 to guide the light to the port 164 or the port 166 in response to a user input received by the input device 180. Referring to FIG. 3, the optical fiber 150 can be coupled to the light source 210, and the optical fiber 140 can be coupled to a light source 240. The light source 240 can direct light to a port 244. The optical fiber 140 can be coupled to the light source 240 at the port 244. The light source 210 can direct light to the port 166. The optical fiber 150 can be coupled to the light source 210 at the port 166. The light source 210 or the light source 240 is configured to output light to selectively illuminate the eye of the patient in response to a user input. For example, the user can select which of the optical fibers 140, 150 transmit light to the surgical field based on a user input received by the input device 180 selecting which of the light sources 210, 240 outputs light. The light source 210 and/or the light source 240 can be in communication with the input device 180.

The light source 210 and/or the light source 240 can include a laser source, a narrowband laser source, a broadband laser source, such as a supercontinuum laser source, an incandescent light bulb, a halogen light bulb, a metal halide light bulb, a xenon light bulb, a mercury vapor light bulb, a light emitting diode (LED), other suitable sources, and/or combinations thereof. For example, the light sources 210, 240 can be configured to output bright, broadband, and/or white light to the surgical field. The light sources 210, 240 can be configured to output any suitable wavelength(s) of light, such as a visible light, infrared light, ultraviolet (UV) light, etc. The light sources 210, 240 can be in communication with optics, such as lenses, mirrors, filters, and/or gratings, configured to vary the wavelength of light. The light sources 210, 240 can be an illumination light source, a diagnostic light source, and/or a therapeutic light source. In that regard, the light sources 210, 240 and/or the optical fibers 140, 150 can be configured to output diagnostic light, treatment light, and/or light to illuminate the surgical field. For example, the optical fiber 140 can output illumination light while the optical fiber 150 outputs diagnostics light or therapeutic light. In another example, the optical fibers 140, 150 can output different types of illumination light. The optical fiber 140 can output broadband, white light, while the optical fiber 150 outputs narrowband laser light. The optical fiber 140 can output visible light, such as white light, while the optical fiber 150 outputs infrared light or UV light. The optical fiber 140 can output narrowband laser light, while the optical fiber 150 outputs broadband laser light, such as light from a supercontinuum laser source.

Referring to FIGS. 7 and 8, the ophthalmic illumination system 100 can include an optical relay 700. The optical relay 700 can be positioned between the light source 210 and the illumination device 110. A single optical fiber 702 can be coupled to the light source 210 and the optical relay 700, and extend between the light source 210 and the optical relay 700. The optical fiber 702 can transmit light from the light source 210 to the optical relay 700. The optical fibers 140, 150 can be coupled to the optical relay 700. The optical relay 700 can be configured to direct the light transmitted by the optical fiber 702 to the optical fibers 140 or the optical fiber 150. The user can selectively direct the light to the optical fiber 140 or the optical fiber 150 using the optical relay 700. For example, the user can provide a user input at the input device 180 such as the controls 810 or 812 of the illumination device 110, the surgical footswitch, or the controls integrated in the surgical console 160. The input device 180 can be in communication with the optical relay 700, such as via computing device 200. The optical relay 700 can include a switch, a butt coupler, any suitable combination of optics, such as lenses, such as a gradient index (GRIN) lens, mirrors, filters, and/or gratings, other suitable components, and/or combinations thereof. For example, the switch of the optical relay 700 can be configured to selectively direct light to the optical fiber or the optical fiber 150 in response to the user input. Implementing the optical fiber 702 and the optical relay 700 can advantageously reduce the distance spanned by the optical fibers 140, 150. Longer optical fibers 140, 150 can be associated with additional expense and additional components for the user to navigate during the ophthalmic surgical procedure.

The optical relay 700 can be positioned at any location between the light source 210 and the illumination device 100, including within the optical fiber 702 and the cannula 130 of the illumination device 110. As illustrated in FIG. 8, the optical relay 700 can be positioned within the body 120 of the illumination device 110. The optical fiber 702 can extend between the light source 210 and the body 120, and the optical fibers 140, 150 can extend between the body 120 and the cannula 130.

Referring to FIGS. 8 and 9, the illumination device 110 can include a deflection mechanism 800 configured to selectively bend, angle, bow, curve, and/or otherwise cause the cannula 130 to obtain a non-linear shape. For example, the cannula 130 can be articulated or otherwise made of up two or more individual components. The multiple, individual components of the cannula can allow for the cannula to be at least temporarily deflected such that the light output by the optical fibers 140, 150 can be directed to any desired anatomy within the surgical field, including anatomy not positioned in front of the distal portion 136 of the cannula 130. For example, the cannula 130 can be selectively deflected to illuminate the periphery of the patient's eye. The distal portion 136, the proximal portion 137, and/or any portion of the cannula 130 between the distal and proximal portions 136, 137 can be articulated and/or deflected. The deflection mechanism 800 can be coupled to one, two, three, four, or more pull wires 802 disposed within the cannula 130. The deflection mechanism 800 can include any suitable components configured to actuate the one or more pull wires 802 to selectively deflect the cannula 130. The cannula 130 can be biased to return to a linear configuration when the pull wires 802 no longer act on the cannula 130. The deflection mechanism 800 can be coupled to and/or disposed within the body 800. The user can control the deflection mechanism 800, including the direction and extent of the deflection of the cannula 130, using the controls 810, 812 of the body 120.

Referring to FIGS. 2, 3, 7, 8, and 9, the ophthalmic illumination system 100 can include a therapeutic light source 220. The therapeutic light source 220 can be part of a therapeutic beam delivery system, such as a laser beam delivery system, a photocoagulation system, a photodynamic therapy system, a retinal laser treatment system. An optical fiber 222 can be coupled to a port 224 of the therapeutic light source 220. The optical fiber 222 can transmit the therapeutic beam to the surgical field, such as the patient's eye. In some cases, one of the optical fibers 140, 150 can be configured to transmit light to illuminate the surgical field while the other of the optical fibers 140, 150 can be configured to transmit therapeutic light. The optical fibers 140, 150 can be optically coupled to the light source 210, the therapeutic light source 220, and/or the light source 240, in such cases.

The ophthalmic illumination system 100 can include an endoscopy subsystem 230. The endoscopy subsystem 230 can be configured to image the surgical field. For example, the user can visualize the surgical field during the surgical procedure using a surgical microscope. The user can view the anatomy being operated on within the eye through the lens of the eye with the surgical microscope. The endoscopy subsystem 230 can be used to visualize the area of the eye being operated on when the user cannot view that area through the lens with the surgical microscope. For example, the lens may be cloudy or the optical path of the surgical microscope may be blocked. The user can also use the endoscopy subsystem 230 to see the periphery of the eye, which may be not visible with the surgical microscope. An endoscopic fiber bundle 232 can be coupled to the endoscopy subsystem 230 at a port 234. The endoscopic fiber bundle 232 can include multiple individual fibers 236. The endoscopic fiber bundle 232 can receive and transmit light reflected from the surgical field. The endoscopy subsystem can generate images based on the received light. The images can be output to a display device 168 in communication with the endoscopy subsystem 230.

The optical fiber 222 associated with the therapeutic light source 220 and the endoscopic fiber bundle 232 associated with the endoscopy subsystem 230 can be coupled to the illumination device 110. For example, the optical fiber 222 and the endoscopic fiber bundle 232 can be coupled to and disposed within the cannula 130. Any suitable fixed or movable coupling, including an adhesive, a mechanical structure, and/or combinations thereof, can be implemented. The diameter 148 of the optical fiber 140, the diameter 158 of the optical fiber 150, the diameter of the optical fiber 222, and the diameter of the endoscopic fiber bundle 232 can allow for the multiple optical fibers to be positioned within the diameter 134 of the cannula 130. Implementing multiple optical fibers within the single illumination device 110 and/or the single cannula 130 can advantageously decrease the number of components the user interacts with during the surgical procedure. As illustrated in FIG. 8, a conduit 820, including include the optical fiber 702, the optical fiber 222, and the endoscopic fiber bundle 232, can extend between the illumination device 110 and a surgical console 160. The conduit 820 can also include the optical fibers 140, 150. The user can control the delivery of the therapeutic beam and/or the endoscopy subsystem 230 using the input device 180, such as the controls 810 or 812 of the illumination device 110, the surgical footswitch, and/or the controls integrated in the surgical console 160.

Referring to FIGS. 1, 2, 3, and 7, the light source 210, the light source 240, the therapeutic light source 220, the endoscopy subsystem 230, a probe subsystem 172, and the computing device 200 can be integrated in the surgical console 160. The surgeon can utilize the surgical console 160 to control one or more parameters associated with the ophthalmic surgical procedure. One or more components of the surgical console 110 can be coupled to and/or disposed within a base housing 162 illustrated in FIG. 1. The base housing 162 can be mobile such that it can be positioned proximate to the patient during the ophthalmic surgical procedure. The base housing 162 can include pneumatic, optical, fluid, and/or electrical supply lines facilitating communication between components of the ophthalmic illumination system 100.

The computing device 200 can be in communication with the input device 180, the light source 210, the light source 240, the therapeutic light source 220, the endoscopy subsystem 230, the probe subsystem 172, and the display device 168. The computing device 200 can be configured transmit control signals to and/or receive input or status signals from the components of the ophthalmic illumination system 100. For example, the computing device 200 can control activation and deactivation of the light sources 210, 240, transmission of light to the ports 164, 166, 244, 246, transmission of light by the optical fibers 140, 150, as well as the intensity, wavelength, and/or other characteristics of light output by the light sources 210, 240. In that regard, the light sources 210, 240 can be in electrical communication with the computing device 200. The computing device 200 can include a processing circuit having a processor 202 and a memory 204. The processor 202 can execute computer instructions, such as those stored on the memory 204, to control various components of the ophthalmic illumination system 100. The processor 202 can be a targeted device controller and/or a microprocessor. The memory 204, such as semiconductor memory, RAM, FRAM, or flash memory, can interface with the processor 202. As such, the processor 202 can write to and read from the memory 204, and perform other common functions associated with managing memory 204. The processing circuit of the computing device 202 can be an integrated circuit with power, input, and output pins capable of performing logic functions.

The computing device 200 can output display data to the display device 168 to display data relating to system operation and performance during an ophthalmic surgical procedure. The display device 168 can also display images generated by the endoscopy subsystem 230. The display device 168 can be a standalone device, integrated in the surgical console 160, and/or in communication with the surgical microscope. For example, the images generated by the endoscopy subsystem 230 can be provided to the user as graphical overlay in a field of view of the surgical microscope.

The probe subsystem 172 can be in electrical communication with the computing device 200. The probe subsystem 172 can include various components facilitating operation of the probe 170. The user can utilize the probe 170 within the surgical field to perform one or more surgical maneuvers. For example, the probe 170 can be a cutting probe, a vitrectomy probe, a phacoemulsification probe, a laser probe, an ablation probe, a vacuum probe, a flushing probe, scissors, forceps, an aspiration device, and/or other suitable surgical device. The probe 170 can be in mechanical, electrical, pneumatic, fluid, and/or other suitable communication with the probe subsystem 172.

The input device 180 can be in communication with the computing device 200. The input device 180 can be configured to allow the user to control ophthalmic illumination system 100, including which of the optical fibers 140, 150 transmit light to illuminate the surgical field, selectively moving the optical fibers 140, 150, activating/deactivating the light sources 210, 240, and/or other features described herein. For example, the user can provide a user input at the input device 180 to cause the light source 210 and/or the light source 240 to selectively output light to the optical fiber 140 or optical fiber 150. The input device 180 can comprise any of a variety of ON/OFF switches, buttons, toggles, wheels, digital controls, touchscreen controls, or other user interface components. The input device 180 can be integrally disposed on the surgical console 160 and/or the illumination device 110. For example, the input device 180 can be the one or more controls 810, 820 of the illumination device 110. The input device 162 can be a distinct component, such as, by way of non-limiting example, a surgical footswitch, a remote control device, a touchscreen control device, and/or another computing device. The ophthalmic illumination system 100 can include multiple input devices 180. The input device 180 can generate and transmit input signals based on the received user input. The computing device 200 can receive and process the input signal. The computing device 200 can generate and transmit control signals to the light source 210, the light source 240, the therapeutic light source 220, the endoscopy subsystem 230, the probe subsystem 172, and the display device 168.

Embodiments as described herein can provide devices, systems, and methods of illuminating the surgical field using light with different angular profiles. Multiple optical fibers respectively sized and shaped to output the light with the different angular profiles can be implemented in an illumination device. The examples provided above can be exemplary in nature and not limiting. One skilled in the art may readily devise other systems consistent with the disclosed embodiments intended to be within the scope of this disclosure. As such, the application can be limited only by the following claims.

The invention claimed is:

1. An ophthalmic illumination apparatus, comprising:
a body sized and shaped for grasping by a user;
a cannula coupled to the body and configured to be positioned within an eye of a patient;
a first optical fiber disposed within the cannula, wherein the first optical fiber comprises a first distal portion configured to transmit light having a first angular profile; and
a second optical fiber disposed within the cannula, wherein the second optical fiber comprises a second distal portion configured to transmit light having a second angular profile; wherein:
the first distal portion and the second distal portion are sized or shaped differently; and
the first angular profile and second angular profile provide different fields of illumination; and
an input device configured to receive, during an ophthalmic surgical procedure, a first user input to cause the first optical fiber to selectively illuminate the eye of the patient with the first angular profile and a second user input to cause the second optical fiber to selectively illuminate the eye of the patient with the second angular profile; wherein:
the first distal portion includes a first tapered tip; and
the second distal portion includes at least one of:
a scattering tip; and
a second tapered tip sized or shaped differently than the first tapered tip.

2. The apparatus of claim 1, wherein:
at least one of the first optical fiber or the second optical fiber is translatable with respect to the cannula.

3. The apparatus of claim 1, further comprising:
a light source coupled to the first optical fiber and the second optical fiber, and configured to output light to selectively illuminate the eye of the patient via the first optical fiber or the second optical fiber.

4. The apparatus of claim 3, further comprising:
an optical relay disposed between a light source and the cannula, wherein the optical relay is configured to selectively direct the light output by the light source to one of the first optical fiber or the second optical fiber in response to at least one of the first or second user input.

5. The apparatus of claim 4, wherein:
the optical relay is disposed within the body.

6. The apparatus of claim 1, further comprising:
a first light source coupled to the first optical fiber; and
a second light source coupled to the second optical fiber;
wherein the first and second light sources are configured to selectively output light to illuminate the eye of the patient in response to at least one of the first or second user input.

7. The apparatus of claim 1, further comprising:
a third optical fiber disposed within the cannula, wherein the third optical fiber is coupled to a therapeutic light source and configured to transmit a therapeutic light beam into the eye of the patient; wherein the therapeutic light source comprises part of a laser beam delivery system, a photocoagulation system, a photodynamic therapy system, or a retinal laser treatment system.

8. The apparatus of claim 1, further comprising:
an endoscopic fiber bundle disposed within the cannula and configured to receive and transmit light reflected from a surgical field to visualize the eye of the patient.

9. The apparatus of claim 1, further comprising:
a deflection mechanism coupled to the cannula and configured to selectively bend the cannula.

10. A method of ophthalmic surgical illumination, the method comprising:
receiving a first user input during an ophthalmic surgical procedure;
in response to the first user input, illuminating an eye of a patient with light having a first angular profile, wherein the light having the first angular profile is transmitted by a first optical fiber disposed within a cannula positioned within the eye, the first optical fiber having a first distal portion configured for the first angular profile;
receiving a second user input during the ophthalmic surgical procedure;
in response to the second user input, illuminating the eye of the patient with light having a second angular profile, wherein the light having the second angular profile is transmitted by a second optical fiber disposed within the cannula, the second optical fiber having a second distal portion configured for the second angular profile; wherein:
the first distal portion and the second distal portion are sized or shaped differently;
the first angular profile and second angular profile provide different fields of illumination;
the first distal portion includes a first tapered tip; and
the second distal portion includes at least one of:
a scattering tip; and
a second tapered tip sized or shaped differently than the first tapered tip.

11. The method of claim 10, further comprising:
receiving the first and second user input at an input device to cause a light source coupled to the first and second optical fibers to output light to a selected one of the first optical fiber or the second optical fiber.

12. The method of claim 10, wherein:
an optical relay disposed between a light source and the cannula selectively directs the light output by the light source to the first optical fiber or the second optical fiber.

13. The method of claim 10, further comprising:
receiving the first and second user input at an input device to cause one of a first light source coupled to the first optical fiber or a second light source coupled to the second optical fiber to selectively output light to illuminate the eye of the patient.

* * * * *